United States Patent [19]

Barbet et al.

[11] Patent Number: 5,274,076
[45] Date of Patent: Dec. 28, 1993

[54] HYDROPHILIC DERIVATIVES, THEIR APPLICATION TO DIAGNOSIS AND TO THERAPEUTICS, DIAGNOSTIC OR THERAPEUTIC KITS AND IMMUNOLOGICAL REAGENTS

[75] Inventors: Jacques Barbet; Michel Delaage, both of Marseilles; Anne Gruaz-Guyon, Boulogne; Jean-Marc Le Doussal, Marseilles, all of France

[73] Assignee: Immunotech Partners, Marseilles, France

[21] Appl. No.: 584,003

[22] Filed: Sep. 18, 1990

[30] Foreign Application Priority Data

Sep. 21, 1989 [FR] France ................. 89 12622

[51] Int. Cl.$^5$ .................. C07K 5/06; C07K 5/08; C07K 5/10; C07C 237/20
[52] U.S. Cl. ..................... 530/330; 424/1.1; 424/2; 435/7.23; 436/512; 436/536; 436/545; 530/331; 562/448
[58] Field of Search ............... 530/331, 330; 514/18, 514/19, 836, 885; 562/448; 424/1.1, 2; 435/7.23; 436/512, 536, 545

[56] References Cited

U.S. PATENT DOCUMENTS 4,331,646  5/1982  Delaage ..................... 514/19

FOREIGN PATENT DOCUMENTS

| 217577 | 4/1987 | European Pat. Off. . |
| 251494 | 1/1988 | European Pat. Off. . |
| 263046 | 4/1988 | European Pat. Off. . |
| 0327365 | 8/1989 | European Pat. Off. . |
| 3679 | 10/1983 | World Int. Prop. O. . |
| 8907114 | 9/1990 | World Int. Prop. O. . |

*Primary Examiner*—Mary E. Ceperley
*Attorney, Agent, or Firm*—Browdy and Neimark

[57] ABSTRACT

Derivatives comprising two hydrophilic haptens and an effector group comprising a radioactive isotope or known to be able to be labelled by a radioactive isotope or comprising an active principle or known to be able to bind an active principle, linked by a connecting bridge application to diagnosis and to therapeutics, diagnostic or therapeutic kits and immunological reagents containing them.

5 Claims, No Drawings

HYDROPHILIC DERIVATIVES, THEIR APPLICATION TO DIAGNOSIS AND TO THERAPEUTICS, DIAGNOSTIC OR THERAPEUTIC KITS AND IMMUNOLOGICAL REAGENTS

The present invention relates to derivatives which can be used especially as immunological reagents intended, in particular, to target animal cells with a view to detecting or to destroying them, reagent kits containing them and their application to the visualisation and destruction of the cells.

French Patent Application No. 86.13146 and European Patent Application No. 87.430031.2 described immunological reagents intended to target animal cell for the detection and destruction thereof in vivo.

These immunological reagents comprise two types of products, namely a) a monoclonal antibody or a fragment of antibody having affinity for a cellular type, a particular tissue or a constituent of an animal organism conjugated with a second antibody or fragment of antibody having affinity for a specific hapten group and b) a molecule composed of at least two identical or different haptens recognised by one of the antibodies and by a moiety formed by a visualisation element, or an product active or known to be able to receive a visualisation element or an active product intended to destroy the target cell.

Product (b) will be designated "probe" in the following.

When it is desired to effect satisfactory visualisation of a target cell, it is desirable for the background noise to be reduced as much as possible. Similarly, in view of the fact that the cytotoxic active principles normally exhibit a certain degree of toxicity, it is desirable to encounter them only at the level of the target cell to be destroyed, as quickly as possible after they have been administered.

It is for this reason that the present invention relates to derivatives characterised in that they comprise two hydrophilic haptens and an effector group comprising a radioactive isotope or known to be able to be labelled by a radioactive isotope or comprising an active principle or a principle known to be able to bind an active principle. These derivatives are analogous to the products described in b) above.

Within the scope of the present invention "hapten" means a molecule capable of being bound specifically to an antibody at the level of one of its binding sites. It is a molecule which is not antigenic by itself but which can become so by covalent binding on to a macromolecule. Its molecular weight is usually lower than 1500 daltons.

The term "hydrophilic" means that the partition coefficient between a neutral aqueous phase (near to physiological conditions) and an organic solvent which is not completely miscible with water, such as N-butanol, is higher than 1 for the isolated hapten. This measurement may be carried out, in particular after agitating for 2 hours a solution of hapten in 10 mM Hepes, 150 mM NaCl, pH 7.4, mixed with an equal portion of butanol.

The preferred haptens according to the present invention have a molecular weight of between 300 and 1500 daltons and include polar chemical groups. Inter alia, these groups are alcohols, amines, carboxylic, sulphonic and phosphoric acids, as well as their esters and amides.

Of the derivatives forming the subject-matter of the present invention those are preferred, characterised in that these haptens have a dissociation constant below or equal to $10^{-5}$ M and, in particular below or equal to $10^{-6}$ M, with an antibody which is specific to them. This constant is determined under normal conditions with respect to pH, temperature and salt concentration.

As indicated in the above-mentioned French Patent Application, the haptens may cover a wide variety of structures. However, particularly preferred haptens are those comprising a chelating group.

The term "chelating" means a molecule which can co-ordinate with a metal atom in a very stable manner.

The most significant chelating groups which are suitable as hydrophilic haptens in accordance with the present invention are poly-amino-carboxylic acids, especially diethylene-triamine-pentaacetic acid (DTPA) and its derivatives.

These chelating groups may or may not contain a metal and those containing complexed indium are particularly preferred.

Preferred haptens also include the derivatives of polar aminoacids, particularly of histidine and the derivatives of histamine, and more particularly histamine-succinyl-glycine. It is also possible to indicate fluorescein and its derivatives, and methotrexate.

In a probe the haptens and the effector group(s) are linked in a stable manner by a connecting bridge. The latter makes it possible to effect the simultaneous binding of at least two specific antibodies on the hapten or haptens of a single probe molecule and, therefore, the formation of the particular complexes desired.

One of the haptens may also serve as an effector; in particular, one of its atoms can be replaced in the probe by a radioisotope or an active principle, such as those described below: one portion of the active principle may also form the hapten. DTPA-indium may be indicated by way of example.

The expression "effector group" means a chemical group responsible for the effect desired, consecutively to the use of the probe, on its target in the organism. The effector group may effect either the detection of the probe accumulation sites or, for example, the destruction of cells at the level of the accumulation sites.

In the first type of application, the effector group comprises, for example, one or more atoms which can be detected by suitable physical means, for example radioactive atoms emitting radiation, in particular gamma radiation It is also possible to indicate the atoms or chemical groups which are sufficiently paramagnetic to interfere with nuclear magnetic resonance signals.

In the second type of application, the effector group could comprise one or more emitters of ionising radiation, for example beta or alpha radiation for the purpose of radiotherapy. It could also comprise one or more chemical groups which by themselves have cytotoxic potential, such as alkylating agents, methotrexate, Vinca alkaloids, anthracyclines or vegetable or bacterial toxins, such as ricin or diphtheria toxin, or under the action of external radiation, such as porphyrins.

The preferred connecting bridges are those which allow adequate separation of haptens, in particular greater than 10 ångströms.

Preferably, these bridges are not very sensitive to hydrolysis once they have been injected into the organism. As connecting bridges there are advantageously used the amino acids, preferably the D series, with peptidic linking For certain special applications, the abovedescribed connecting bridges comprise a phenol group and more particularly the connecting bridges containing tyrosine or tyrosine constituents are preferred.

The derivatives forming the subject-matter of the present invention preferably also include those whose haptens are glycyl-succinyl-histamine, which are coupled to a phenolic diamine, in particular coupled to a peptide containing tyrosine.

Preferred derivatives according to the present invention include more particularly the following derivatives of tyrosine:

N-α-DTPA-tyrosyl-N-ε-DTPA-lysine;
N-α-N-ε-di-(DTPA-glycyl)-lysyl-tyrosine;
N-α-N-ε-di-(histamine-succinyl-glycyl) lysyl-tyrosine of the respective formulae:

in a single molecule by any chemical or enzymatic procedure. Those procedures that result in a uniquely defined chemical structure are preferred. Structures in which the distance between two hapten groups may be larger than 25Å are also preferred. An example of suitable chemical structure is provided by peptides of small molecular weight whose side chains and terminal amino and/or carboxylate residues are substituted by the haptens and the effector groups. Peptides which contains one or several D-amino acids are preferred. Preferred chemical structure is one which allows radiolabeling with a radioisotope suitable for radioimmunoimaging or radioimmunotherapy. Most preferred structures are those in which a phenol or phenyl group is present. In that case, labeling may be performed with radioactive isotopes of the halogens such as, for example, $^{18}F$, $^{76}Br$, $^{77}Br$, $^{123}I$, $^{125}I$, $^{131}I$, $^{211}At$. In that case too, preferred radioactive isotopes are $^{123}I$ for diagnosis and $^{131}I$ or

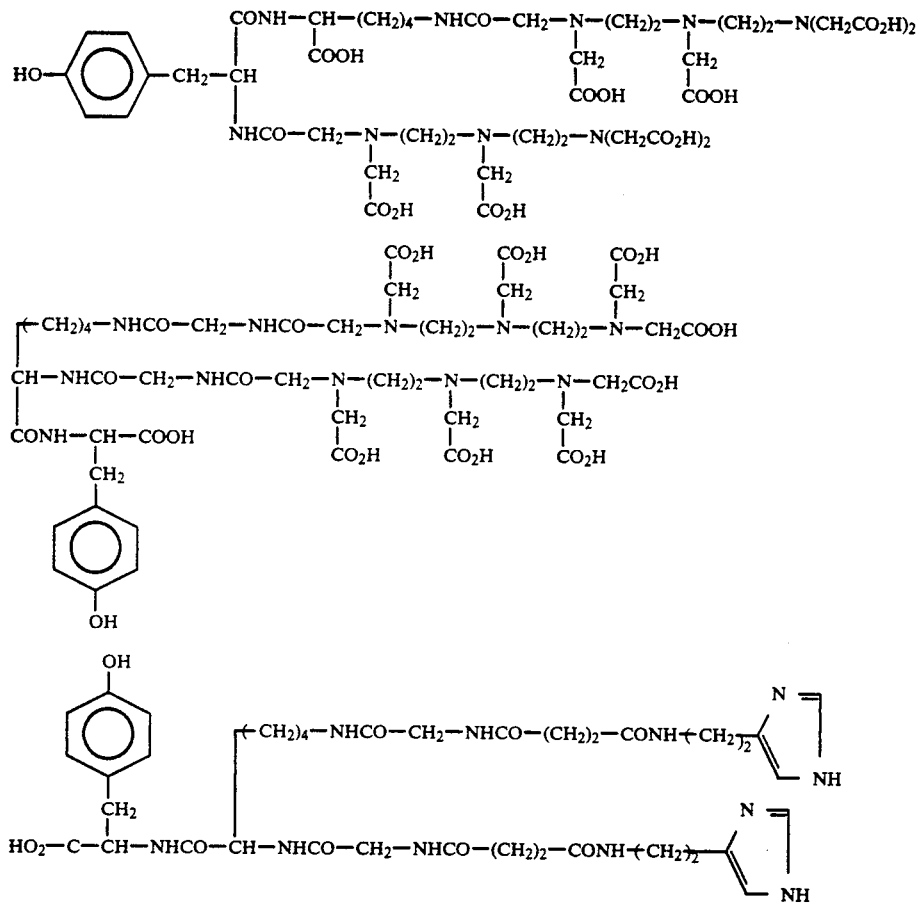

The derivatives described above exhibit remarkable properties as a result of two hydrophilic hapten groups and their effector group.

It is for this reason that the present application also relates to the application of derivatives of the type defined above to diagnosis and therapeutics.

Any hapten to which monoclonal antibodies are available or may be produced may be suitable for the present invention. Those haptens which are not present in human tissues are preferred. Are also preferred haptens which are not degraded too rapidly after in vivo administration and those which do not present too high a toxicity to animals or human. Two or more haptens and at least one effector group may be linked together $^{211}At$ for therapy. Other most preferred structures are those in which one or several chelating group have been introduced. In that case, a radioactive metal cation may be used as a label, such as, for example, $^{57}Co$, $^{67}Ga$, $^{68}Ga$, $^{67}Cu$, $^{90}Y$, $^{97}Ru$, $^{99m}Tc$, $^{111}In$, $^{113m}In$, $^{203}Pb$, $^{212}Bi$. In that case too, preferred radioactive isotopes are $^{111}In$ or $^{99m}Tc$ for diagnosis and $^{90}Y$ or $^{212}Bi$ for therapy.

In another aspect of the invention, a stable paramagnetic ion, such as Gd, Fe, Mn, may be used. Another suitable structure is one which carries one or several paramagnetic compounds such as, for instance, paramagnetic ions (e.g. Gd, Fe, or other heavy metals), or stable free radicals (e.g. derivatives of the nitroxide radical). Superparamagnetic complexes such as those produced by precipitation of magnetite in the presence of dextran are also suitable (Ohgushi et al.)

Alternatively, the radiolabeled or paramagnetic moiety of the tracer may serve as a hapten, as, for instance, when a chelating agent is used to bind $^{111}$In, $^{99m}$Tc, or a stable paramagnetic metal such as Gd, or any other metal isotope. In that case, two or more chelated metals should be included into the tracer molecule.

In all cases, the radioactive or stable isotope may be introduced after the synthesis of the nonlabeled tracer has been completed, as in the case of tyrosine radioiodination or radioisotopic metal chelation, or before.

Still another suitable structure is one which associates in the same molecule two or more haptens and one or several molecules of cytotoxic drug or toxin. Preferred cytotoxic drug are methotrexate, a derivative of the antitumor Vinca alkaloids, or of the platinum complexes, or of the anthracycline. A suitable toxin may be a plant or bacterial toxin or its separated toxic A chain, such as diphtheria toxin, ricin, abrin, gelonin, or pokeweed antiviral protein.

With a view to their diagnostic use, the derivatives according to the present invention may, for example, be injected intravenously in humans or animals.

At the same time as or before injection of the probe (for example from a few minutes up to several hours before, preferably 12 to 48 hours), there is injected a bispecific antibody conjugate composed of an antibody, in particular monoclonal, or a fragment of antibody, likewise preferably monoclonal, specific to a cell or normal or pathological component of a live being, in particular of a human, coupled to an antibody, in particular monoclonal, or a fragment of antibody, preferably specific to the hapten in question, as described below as product a), for example in a dose of 0.1 mg to 1 g according to the probe used and, preferably, from 1 to 100 mg in an adult human.

Derivative a) can be used alone or as part of a mixture (cocktail), each having a particular specificity to different normal or pathological cells or constituents of the organism and a specificity to the same hapten.

After injection of the derivatives according to the invention, measurement or detection is carried out using instruments well known in the art, for example for scintigraphy or NMR imaging.

In the case of isotopic diagnosis, for example, an activity of from 0.1 to 100 mCi and more particularly from 3 to 10 mCi is applied.

Similarly, it is possible to carry out the localised treatment of a disease, tumoral for example, using a probe in accordance with the present invention, having as effector a suitable active principle, in particular cytotoxic.

The dosage will then be limited by the secondary toxicity of the active principle on normal organs and, in particular, on the bone marrow.

For a radioimmunotherapy application, the preferred dose will, for example, be between 50 mCi and 1 Ci.

Taking into account the special use of the derivatives according to the present invention, the subject-matter of the present application also concerns diagnostic or therapeutic kits, characterised in that they contain at least one of the derivatives according to the present invention, such as those defined above and an antibody or fragment of antibody, in particular monoclonal, recognising a cell type or a particular tissue, conjugated with a second antibody or fragment of antibody recognising a hapten group of said derivative.

Finally, the present application relates to immunological reagents comprising a conjugate, comprising an antibody or fragment of antibody, in particular monoclonal, having an affinity for a particular cell type or a normal or pathological constituent of the particular organism, coupled to an antibody or fragment of antibody, in particular monoclonal, having an affinity for a given hapten, and a synthetic molecule comprising at least two haptens corresponding to the above conjugate and to at least one site, suitable for radioactive labelling or for binding an active principle, bound in covalent manner, characterised in that the synthetic molecule is an above-defined derivative.

The mention of antibody conjugate is not prejudicial to any method of preparation insofar it also relates to bispecific antibodies, also designated recombinant, quadromes or polydomes, for example.

The following examples illustrate the present invention without implying any limitation thereof.

EXAMPLE 1

N-α-DTPA-tyrosyl-N-ε-DTPA-lysine

45 μMol of tyrosyl-lysine are dissolved in 600 μl of water, added to 45 μmol of triethylamine and 180 μmol of cyclic anhydride of DTPA in solution in 1 ml of DMSO.

It is left for 16 hours at ambient temperature, the pH being maintained at about 7 using triethylamine. It is purified by gel filtration (Biogel P4 column). The fractions corresponding to the expected product are recovered and they are purified on an ion-exchange column (mono-Q Pharmacia) and high-pressure liquid chromatography using a C-18 column.

The resultant product is identified by UV spectrometry (max 277 nm) and mass spectrometry (molecular peak 1060).

EXAMPLE 2

N-α-N-ε-di-(DTPA-glycyl)-lysyl-tyrosine

Starting with 1 g of N-α-BOC-O-benzyl-L-tyrosine, N-α-N-ε-di-(glycyl)-lysyl-tyrosine is prepared in conventional manner by solid phase synthesis.

The resultant product is liberated using liquid hydrofluoric acid and it is purified by gel filtration and high-pressure liquid chromatography. This peptide is then reacted with DTPA cyclic anhydride, as described above in Example 1; the resultant product is purified by gel filtration, by chromatography on an ion-exchange column and high-pressure liquid chromatography; it is identified in the manner described above (max 277 nm, molecular peak 1174).

EXAMPLE 3

N-α-N-ε-di-(histamine-succinyl-glycyl)-lysyl-tyrosine

N-α-N-ε-di-(glycyl)-lysyl-tyrosine is synthesized on the resin as described in Example 2. After deprotection of the terminal amino groups, 2.5 equivalents of succinic anhydride in DMF and 2.5 equivalents of triethylamine are added to the resin. It is left for 2 hours at ambient temperature, washed and 2.6 equivalents of histamine and BOP in solution in DMF and 3.5 equivalents of diisopropyl-ethylamine are added.

It is allowed to incubate again and the desired product is liberated; it is purified by gel filtration and by high-pressure liquid chromatography and the resultant product is identified by UV spectrometry (max 220 nm and 277 nm) and mass spectrometry (molecular peak 810).

EXAMPLE 4

Labelling of the derivative of Example 1 with indium-111

The product of Example 1 is diluted to 0.5 μM in 100 mM acetate and 10 mM citrate buffer at pH 5. 0.5 mCi of indium-111 trichloride (in 50 μl of 50 mM hydrochlorid acid) is added to 50 μl of the above solution and it is left to incubate for 16 hours at 37° C.

Excess non-radioactive $InCl_3$ (10 μl of a 1 mM solution in 100 mM citrate buffer at pH 5) is then added to saturate the two chelating groups of the derivative of Example 1.

The labelled derivative of Example 1 is diluted to the required activity immediately prior to injection using a 20 mM Hepes, 150 mM HCl, 10 μM EDTA pH 7.4 solution.

EXAMPLE 5

Radioimmunoscintigraphy of human melanoma grafted on to nude mice with anti-melanoma anti-DTPA indium dual specificity conjugates and N-α-DTPA-tyrosyl-N-ε-DTPA-lysine labelled with indium 111.

$3.10^6$ human melanoma cells (A375) are injected subcutaneously into the abdomen of nude mice. 3 to 4 weeks later the mice develop tumours of 0.5 to 2 g. The mice are then injected with 2 to 10 μg of dual specificity conjugate prepared by chemical coupling of the F(ab)'$_2$ fragment of a human anti-melanoma antibody (mouse monoclonal antibody IgG$_1$, kappa) to the reduced F(ab)'$_2$ fragment of an anti-DTPA-indium antibody (mouse monoclonal antibody IgG$_1$, lambda) using the heterobifunctional reagent EMCS.

Twenty four hours later, mice are injected with 10 μCi of the derivative of Example 1 labelled with indium-111. Images are then produced at selected time intervals using a Sopha Medical Gammatome 2 gamma camera equipped with a medium energy high-resolution collimator or the animals are killed and the major organs and the tumour are measured for radioactivity associated with indium-111 using a gamma counter.

Only a few minutes after injection of the labelled derivative of Example 1 it is possible for tumours to be observed on the images produced by the gamma camera. It is ascertained that a large majority of the circulating radioactivity is eliminated in less than 24 hours, whereas the radioactivity bound to the tumour is established within a few hours and remains stable for at least two days.

Non-specific accumulation of radioactivity was essentially limited to the kidneys.

Radioactivity measured after 24 hours in the organs and tumours indicates a high tumour/organ ratio (T/O>3) in all organs, except for the kidneys (T/O=0.7).

Tumour binding was specific, in view of the fact that the tumours did not accumulate significant amounts of radioactivity without injection of dual specificity antibody conjugates or if the conjugate was specific for an antigen associated with another tumour. If indium-111-labelled DTPA (an monovalent analogue of the derivative of Example 1 recognised with high affinity by the anti-indium-DTPA) is injected instead of the derivative of Example 1, radioactivity is excreted very rapidly and little specific binding is observed.

When the directly labelled F(ab)'$_2$ fragment of the anti-melanoma antibody is injected, specific binding to the tumour is observed but the circulating radioactivity is eliminated more slowly and the tumour/organ ratios in 24 hours are lower (between 0.4 and 7). Non-specific binding in the kidneys and liver is particularly high (T/O=0.4 and 1.5 respectively).

In conclusion, the derivatives according to the present invention give remarkable results in relation to other direct and indirect visualisation techniques.

EXAMPLE 6

Tolerance to probes in animals

Doses corresponding to 10 nanomoles, i.e. about 10,000 times more than the dose required for radioimmunoscintigraphy, of compounds 1 and 2 previously complexed with non-radioactive indium and compound 3 are administered to BALB/c mice. These mice are then observed for 16 days under normal breeding conditions. No sign of toxicity is observed and the weight gain of these animals is not significantly different from that of a batch of control animals.

EXAMPLE 7

Comparison between compound 1 labelled with indium-111 and di-(DNP-lys)-DTPA in the labelling of tumours in mice.

Experiments are carried out as in Example 5 but the mice are given indium-111-labelled di-(DNP-lys)-DTPA (derivative 1 of French Patent Application 86.13146) instead of the derivative 1 described above. Three hours after injection of the probe, the mice are dissected and the gamma radioactivity of the major organs and tumour is counted. It is observed that the tumour accumulates a dose of radioactivity equivalent to that Obtained with the two compounds of Example 1 of the present invention. However, the elimination of the excess radioactivity is substantially more rapid with the compounds of the present invention, as shown by the following table:

| | Contrast cpm/g in the tumour/cpm/g in the organ 3 hours after injection of the radiolabelled probe | |
|---|---|---|
| Organ | Novel probe derivative of Example 1 | existing probe derivative of of the prior art |
| Plasma | 1.7 | 0.2 |
| Kidneys | 3.5 | 1.0 |
| Liver | 10.8 | 1.3 |
| Spleen | 12.7 | 1.8 |
| Lung | 8.2 | 0.9 |
| Heart | 14.9 | 2.1 |

Accordingly, the tumour to organ contrast is much better with the derivatives of the present invention than with those of the prior art.

EXAMPLE 8

N-α-acetyl, N-ε-DTPA, L-lysyl-L-tyrosyl-N-ε-DTPA-L-lysyl-amide.

The desired product, identified as above (max 277 nm, molecular peak 1228), is prepared using the same procedure as indicated in Example 2.

This derivative has very similar properties to those of the product in Example 1.

EXAMPLE 9

N-α-acetyl, N-ε-(histamine-succinyl-glycyl)-L-lysyl-L-tyrosyl-N-ε-(histamine-succinyl-glycyl)-L-lysyl-amide.

The expected product, identified as above (max 220 and 277 nm, and molecular peak 978), is prepared using the same procedure as indicated in Example 3.

We claim:

1. N-α-DTPA-tyrosyl-N-ε-DTPA-lysine.
2. N-α-N-ε-di-(DTPA-glycyl)-lysyl-tyrosine.
3. N-α-N-ε-di-(histamine-succinyl-glycyl)-lysyl-tyrosine.
4. N-α-acetyl, N-ε-DTPA, L-lysyl-L-tyrosyl-N-ε-DTPA-L-lysyl-amide.
5. N-α-acetyl, N-ε-(histamine-succinyl-glycyl)-L-lysyl-L-tyrosyl-N-ε-(histamine-succinyl-glycyl)-L-lysyl-amide.

* * * * *